(12) United States Patent
Atia et al.

(10) Patent No.: US 7,671,981 B1
(45) Date of Patent: Mar. 2, 2010

(54) SYSTEM FOR SPECTROSCOPIC CARPET IDENTIFICATION

(75) Inventors: Walid A. Atia, Lexington, MA (US); Dale C. Flanders, Lexington, MA (US); Robert K. Jenner, South Hamilton, MA (US); Lawrence P. McDermott, Groton, MA (US); Bartley C. Johnson, North Andover, MA (US)

(73) Assignee: Axsun Technologies, Inc., Billerica, MA (US)

( * ) Notice: Subject to any disclaimer, the term of this patent is extended or adjusted under 35 U.S.C. 154(b) by 124 days.

(21) Appl. No.: 11/769,488

(22) Filed: Jun. 27, 2007

Related U.S. Application Data

(60) Provisional application No. 60/805,905, filed on Jun. 27, 2006.

(51) Int. Cl.
*G01N 21/00* (2006.01)

(52) U.S. Cl. .................. 356/237.5; 356/237.2

(58) Field of Classification Search ... 356/237.1–237.6, 356/519, 480, 454; 241/24.12, 24.13, 79; 250/339.01–339.12, 341.1, 341.8; 209/3.1, 209/3.3, 547, 583; 372/98
See application file for complete search history.

(56) References Cited

U.S. PATENT DOCUMENTS

| | | | |
|---|---|---|---|
| 5,952,660 A | 9/1999 | Kip et al. | |
| 6,953,119 B1 | 10/2005 | Wening | |
| 2004/0100686 A1 | 5/2004 | Flanders et al. | |
| 2005/0083533 A1 | 4/2005 | Atia et al. | |
| 2005/0206029 A1* | 9/2005 | Moore et al. | 264/143 |
| 2006/0072632 A1 | 4/2006 | Flanders et al. | |
| 2006/0215713 A1 | 9/2006 | Flanders et al. | |

\* cited by examiner

*Primary Examiner*—Gregory J Toatley, Jr.
*Assistant Examiner*—Tri T Ton
(74) *Attorney, Agent, or Firm*—Houston Eliseeva LLP

(57) ABSTRACT

A tunable laser spectroscopic carpet identification system comprises a tunable laser spectroscopy system for generating a tunable signal that is transmitted to a carpet sample. The system detects the tunable signal after interaction with the carpet sample so that an analyzer is able to relate a spectral response of the carpet sample to a chemical composition of the carpet sample. In one example, the spectroscopy system comprises a laser cavity in which the tunable signal is generated, a semiconductor gain medium in the laser cavity, and a tunable element for controlling a wavelength of tunable signal generated in the laser cavity. To deal with variations in water content, the analyzer estimates a water content of the carpet sample using the spectral response of the carpet sample and then determines the chemical composition of the carpet sample in part based on the estimate of the water content.

19 Claims, 6 Drawing Sheets

SYSTEM FOR SPECTROSCOPIC CARPET IDENTIFICATION

RELATED APPLICATIONS

This application claims the benefit under 35 USC 119(e) of U.S. Provisional Application No. 60/805,905, filed on Jun. 27, 2006, which is incorporated herein by reference in its entirety.

BACKGROUND OF THE INVENTION

With increasing raw material costs, the recycling of used carpet becomes increasingly cost effective and even profitable. Carpet is typically composed of a hydrocarbon-based material or natural fibers, such as wool. These types of materials can be effectively recycled.

Typically, when carpet is being recycled, its composition must be determined in a first step in recycling. Carpets based on natural products such as wool must be processed differently from hydrocarbon-based materials. And, carpets based on different types of hydrocarbons must also be separately processed in order to make the recycling as profitable and efficient as possible.

In the past, different techniques have been used to determine the composition of the carpets. One of the most primitive ways of determining the carpet composition is by burning a sample and then determining content based upon the smell and/or character of the flame. This approach has obvious drawbacks. A more sophisticated approach works by determining the spectroscopic response. Specifically, Fourier Transform-Infrared (FT-IR) systems have been used to determine the spectral response of carpet, which response is used to determine the composition of the carpet so that it can be processed accordingly.

SUMMARY OF THE INVENTION

In general, according to one aspect, the invention features a tunable laser spectroscopic carpet identification system. This system comprises a tunable laser spectroscopy system for generating a tunable signal that is transmitted to a carpet sample. The tunable signal is detected after interaction with the carpet sample. Often these systems work in a transmission mode or in a diffuse reflectance mode. An analyzer then relates the spectral response of the carpet sample to a chemical composition of that carpet sample.

In the preferred embodiment, the spectroscopy system comprises a laser cavity in which the tunable signal is generated. A semiconductor gain medium is located in the laser cavity in order to provide amplification. A tuning element controls a wavelength of the tunable signal generated in the laser cavity. In the preferred embodiment, an external cavity laser (ECL) semiconductor system is used.

Presently, the semiconductor gain medium is a semiconductor optical amplifier, specifically a reflective semiconductor optical amplifier, and the tunable element is a Fabry-Perot tunable filter and specifically a microelectricalmechanical system (MEMS) Fabry-Perot tunable filter.

The water content of the carpet samples can vary. Often, in the recycling context, it may be due to water damage that the carpet is being recycled. For systems operating in the near-infrared, where water can have a substantial spectral response, it is important to compensate for the water content of the sample in order to improve the accuracy the chemical composition determination.

In the preferred embodiment, the analyzer estimates a water content of the carpet sample and determines the chemical composition of the carpet sample in part based on the estimate of the water content, specifically by removing the spectral contribution of the water.

In the preferred embodiment, the tunable signal is generated in the near-infrared wavelengths. Specifically, in one embodiment, the tunable signal scans over a scan band extending from about 1550 nanometers to 1800 nanometers. In another embodiment, the tunable signal scans over a smaller scan band stretching from about 1600 nanometers to 1775 nanometers. In still a further embodiment, the tunable laser scans only over wavelengths greater than about 1700 nanometers.

In general, according to another aspect, the invention features a spectroscopic carpet identification system. This system comprises a spectroscopic system for determining a spectral response of the carpet sample. An analyzer relates the spectral response of the carpet sample to a chemical composition of the carpet sample. The analyzer estimates a water content of the carpet sample using the spectral response of the carpet sample and then determines the chemical composition of the carpet sample in part based upon the estimated water content.

In general, according to another aspect, the invention also features a spectroscopic carpet identification method. This method comprises determining a spectral response of the carpet sample and then determining a water content of the carpet sample. The determined water content and the raw spectral response of the carpet sample are then used to determine a chemical composition of the carpet sample.

Finally, in general, according to still another aspect, the invention features a carpet processing method. This comprises determining a spectral response of a carpet sample at a point of carpet removal. In one example, the carpet is being removed from an office or a residence. The chemical composition of the carpet sample is then determined at or near this point of removal. Then, the carpet is labeled at the point of removal to indicate its chemical composition. In one example, this can be simply a handwritten label. In other examples, a barcode label is affixed to the carpet. Then, after the carpet is transported to the processing center to begin recycling, the carpet is processed based on the labeling. In this way, the carpet is labeled at the point of removal where it is easiest to determine the carpet composition and other samples that have similar composition. As a result, processing can be performed more efficiently at the processing center.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
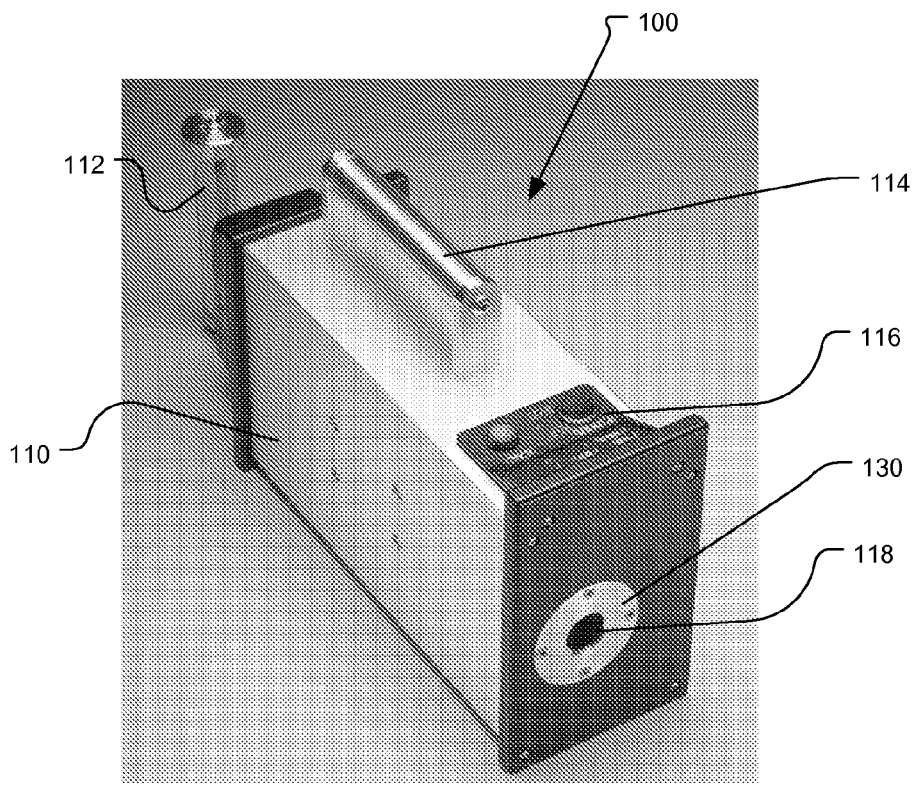
FIGS. 1 and 2 are front prospective and close up control panel detailed views of a tunable laser spectroscopic carpet identification system according to the present invention.
Figure 2:
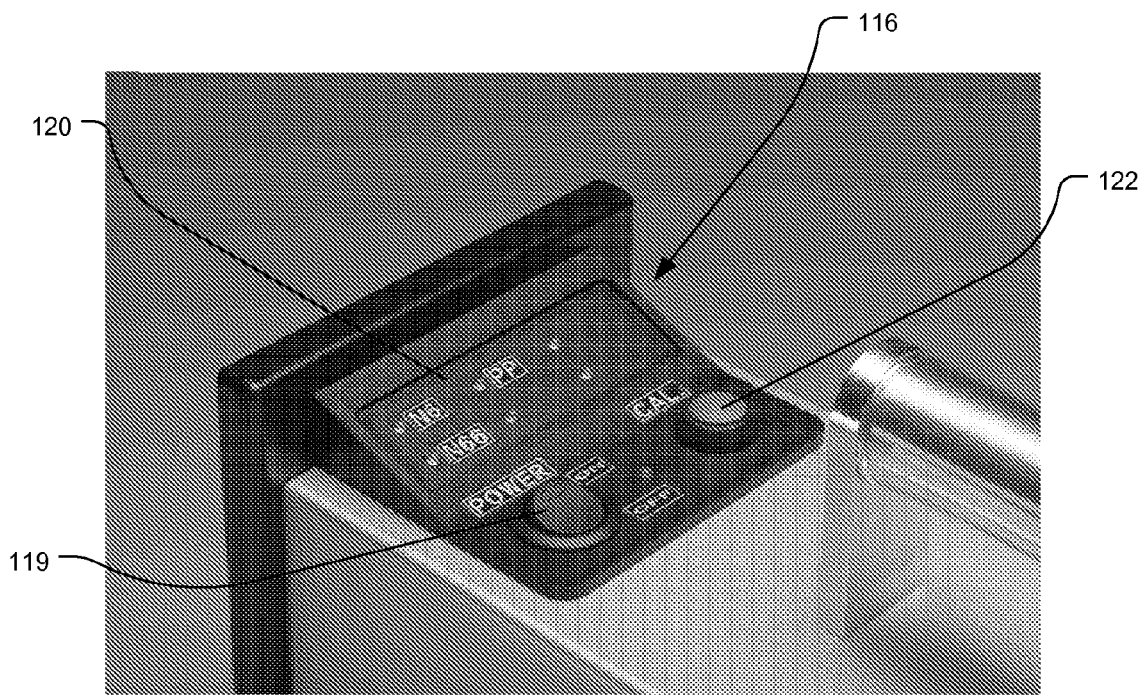

FIGS. 1 and 2 are front prospective and close up control panel detailed views of a tunable laser spectroscopic carpet identification system 100, which has been constructed according to the principles of the present invention.

Specifically, the carpet analyzer 100 comprises a housing 110 that has generally rectangular cross-sections. The housing 110 has two handles 112 and 114. Handle 112 allows the analyzer to be grasped by a person in an upright position and then scanned over a carpet lying on the floor. Handle 114 is used for bringing the analyzer near to carpet possibly in front of the operator.

The control panel 116 is the user interface for operating the carpet ID system 100. The optical port 118 of the carpet ID system 100 emits a tunable signal, which is then detected by a detector in the port 118 defined by ring 130. It thus, emits the tunable signal and detects the diffusely reflected response of the carpet for example to thereby determine the spectroscopic response of the carpet.

FIG. 2 shows the close up view of the control panel/user interface 116 for the carpet ID system 100. It has a power button 119 for powering-on and powering-off the system 100. A calibrate button 122 is used to zero or calibrate the system preferably typically against a substance with a known spectral response. In one example, a door closes over the port 118. On the backside, i.e., inside of the door, a known reflector, such as gold is deposited. In the current embodiment, reflector material such as a thermoplastic resin that has high diffuse reflectance in the near infrared (NIR) range is used. Examples include Spectralon and OPDIMA reflectance materials.

In operation, lights 120 of the user interface panel 116 are lit depending on the spectral response and whether it most closely matches various carpet substances such as polypropylene, nylon 6, nylon 6, 6. In other embodiments, a voice enunciator and/or digital display are used to communication the match information to the operator.

Figure 3:
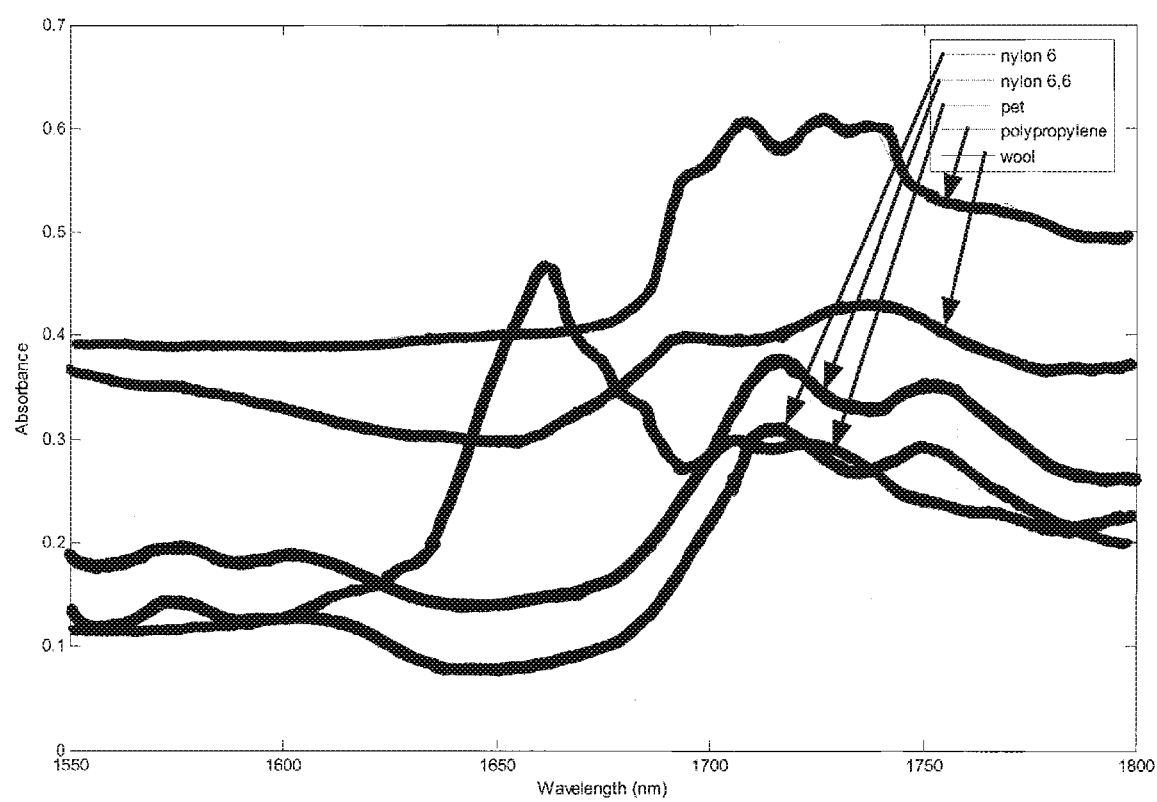
FIG. 3 is a plot of absorbance as a function wavelength (nanometers) for chemical compositions used in common carpeting.

FIG. 3 illustrates the spectral response of different chemicals used in carpets. Specifically, the system determines the spectral response of a carpet sample adjacent the port 118 and then compares the spectral response to nylon 6, nylon 6, 6, PET, polypropylene and wool. The lights are then lit on the user interface to indicate a closest match or the system's inability to find a match based on these stored spectra.

FIG. 3 also illustrates the wavelength of operation in the preferred configuration. Specifically, the tunable signal is scanned over the spectral range of about 1550 to 1800 nanometers. In other embodiments, a smaller range of about 1600 nanometer to about 1775 nanometers is used. In these ranges, the carpet materials such as nylon 6, nylon 6,6 PET, polypropylene, and wool are spectrally distinguishable.

In another embodiment, the system scans for wavelengths greater than only about 1700 nanometers. In one embodiment, the system scans in two bands to identify and distinguish between carpet material nylon 6 and carpet material nylon 6, 6.

Figure 4:
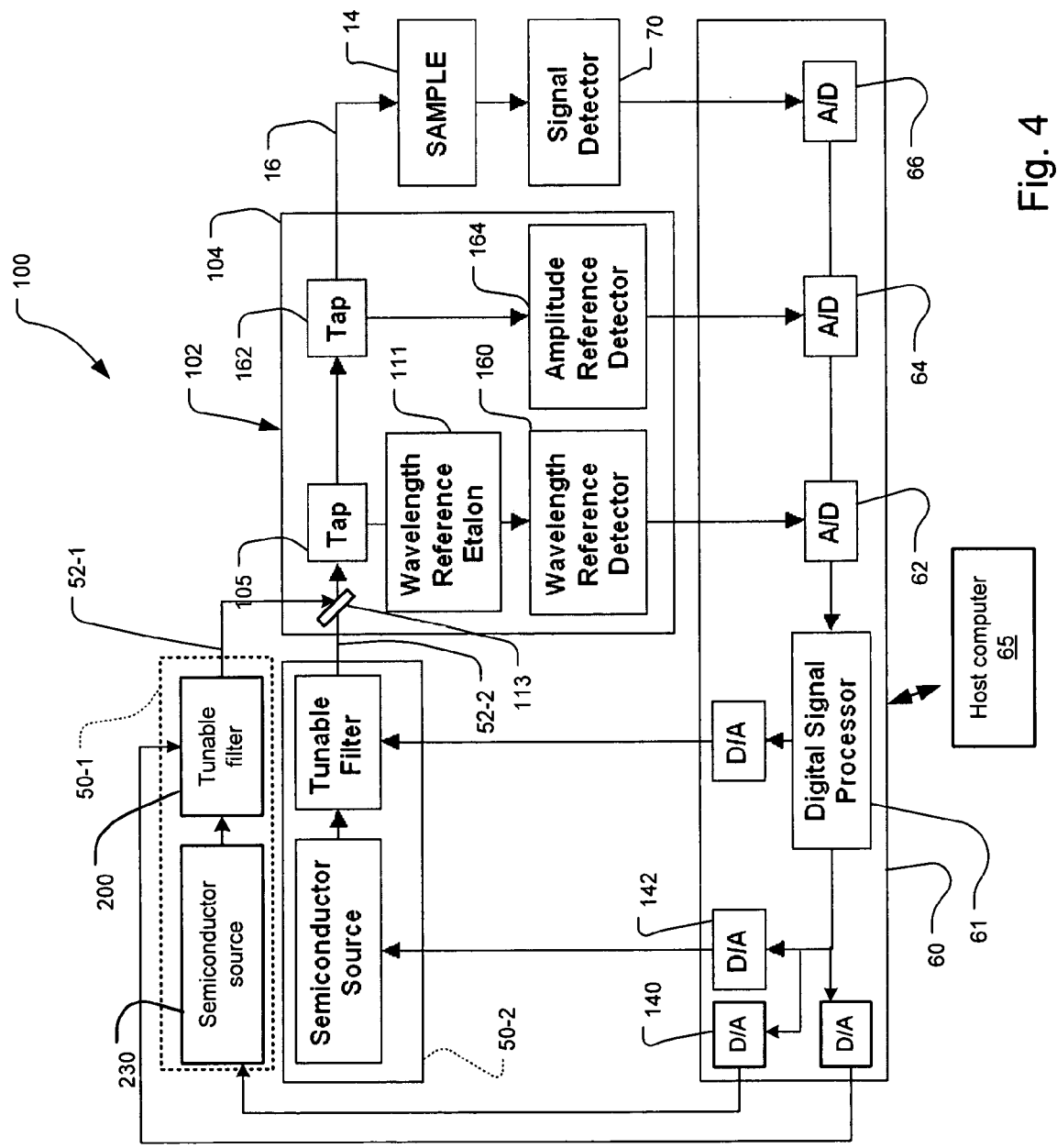
FIG. 4 is a block diagram of a tunable laser spectroscopy system used in an embodiment of the present invention.

FIG. 4 shows the spectroscopy system 100 according to one embodiment. This system is discussed in more detail in U.S. patent application Ser. No. 11/419,993, filed May 23, 2006, by Flanders, et al., which is incorporated herein by this reference in its entirety.

In one embodiment, one or two tunable semiconductor sources 50-1 and 50-2 are provided to generate tunable signals in different, adjacent spectral bands to increase spectral range. In a current embodiment, however, only a single source is used that emits in the range from 1550 to 1800 nanometers (nm). The tunable sources 50-1, 50-2 have corresponding semiconductor chips 230 that are paired with microelectromechanical (MEMS) Fabry Perot tunable filters 200 to create external cavity tunable lasers (ECL).

Each of semiconductor sources 230 and tunable filters 200 of the tunable sources 50-1, 50-2 are controlled by a system controller/analyzer 60. Specifically a digital signal processor core 61 drives the sources and tunable filters via separate digital to analog converters D/A 140, 142.

Respective single mode optical fibers 52-1 and 52-2 carry the tunable signals from each of the sources 50-1, 50-2.

A wavelength amplitude referencing system 102 combines the tunable signals from each of the sources 50-1, 50-2 onto the output fiber 16 while also performing amplitude and wavelength detection.

In more detail, a polarizing beam combiner 113 is used to combine the tunable signals for each of the sources. A wavelength reference tap 105 directs a portion of the combined beam to a quartz reference etalon 111 and a wavelength reference detector 160. An amplitude reference tap 162 directs a portion of the combined beam to an amplitude reference detector 164. Each of these detectors 160, 164 is monitored by the system controller/analyzer 60 via separate analog to digital converters 62, 64.

In operation, the tunable filters 200 are continuously scanned over the spectral scan band. The tunable signal is transmitted to the carpet sample of interest 14 via the output optical fiber 16. The tunable signal from the sample is then detected by signal detector 70 and then digitized by the detector's analog to digital converter 66. In one embodiment, the typical measurement time is less than 2 seconds (with signal averaging). The digital to analog converter 66 samples the detector 70 to provide a resolution of greater than 3.5 cm$^{-1}$.

In the preferred embodiment, every point of every scan is referenced. As the sources 50-1, 50-2 of the spectrometer scan, the signal from the wavelength reference detector 160 is a fringe pattern, analogous to the He—Ne reference signal in an FT-IR. This provides real-time wavelength referencing.

An optical bench 104 on which the reference system 102 is implemented is thermostat-controlled, ensuring both short- and long-term dimensional stability for the etalon 111, and thus both short- and long-term wavelength reproducibility.

Figure 5:
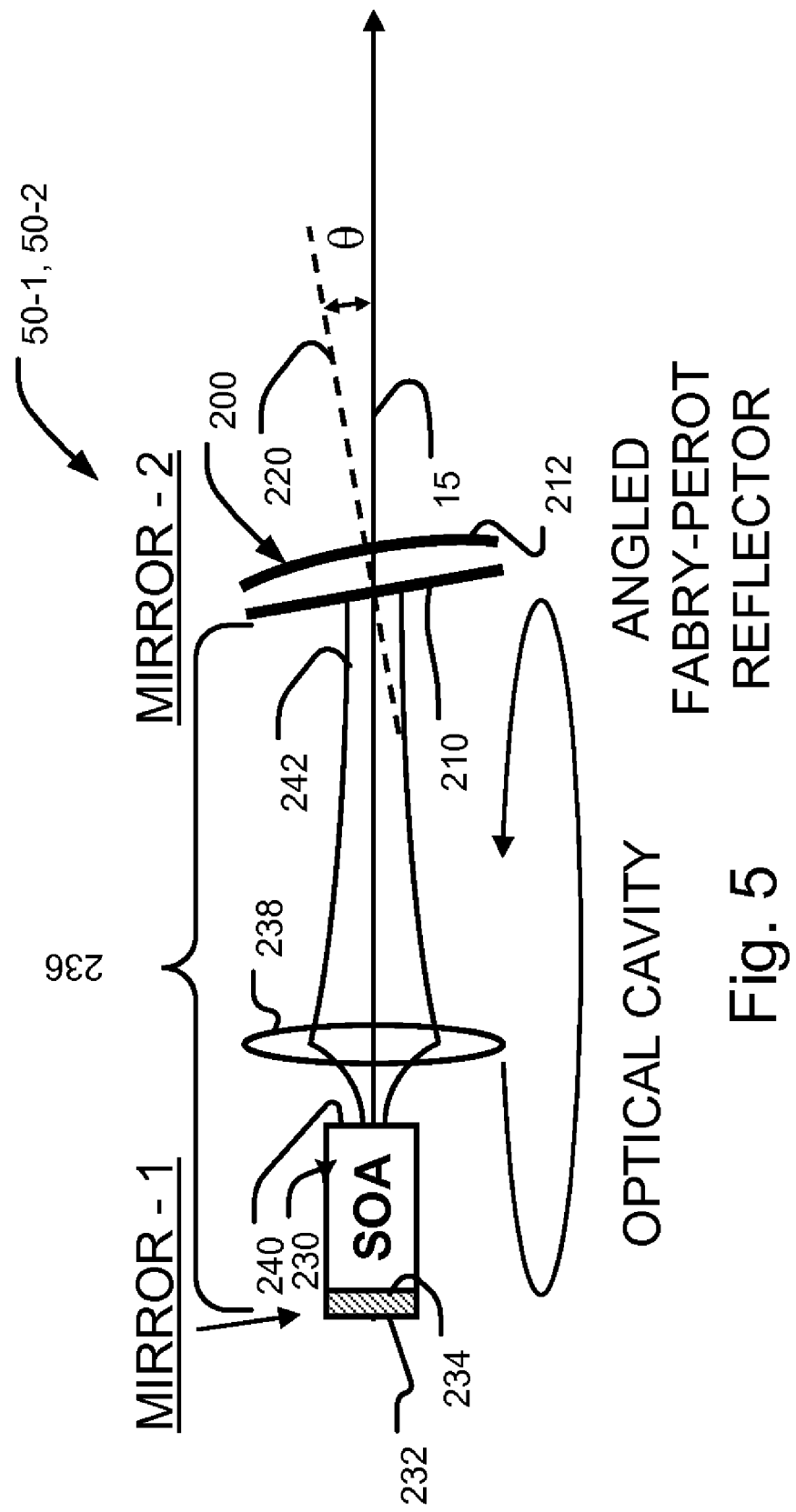
FIG. 5 is a schematic diagram of a tunable external cavity laser used in an embodiment of the present invention.

FIG. 5 illustrates an embodiment of the tunable ECL's in the tunable sources 50-1, 50-2. This ECL system is discussed in more detail in U.S. patent application Ser. No. 11/158,617, filed Jun. 22, 2005, by Flanders, et al., U.S. Pat. Publ. No. US 2006/0215713 A1, which is incorporated herein by this reference in its entirety.

In a current embodiment, a reflective semiconductor optical amplifier (SOA) 230 is used. As a result, a first mirror of the laser cavity 236 is a facet 234 of the SOA gain chip 230 that has a highly reflecting (HR) coating 232. The other mirror of the laser cavity 236 is provided by an angled MEMS Fabry-Perot tunable filter 200 comprising an opposed curved mirror 212 and a flat mirror 210 having an optical axis 220 at angle θ to the axis of the cavity. An intracavity lens 238 is used to collimate or collect the light from an AR coated facet 240 of the SOA 230 and generally form a beam waist 242 to launch the light into the resonant filter 200 and then couple light from the filter 200 back into the chip 230.

In this example, the light output from the laser cavity 236 is provided to the output fiber 15, which is single mode fiber with polarization control such as polarization maintaining or other polarization controlling fiber.

Figure 6:
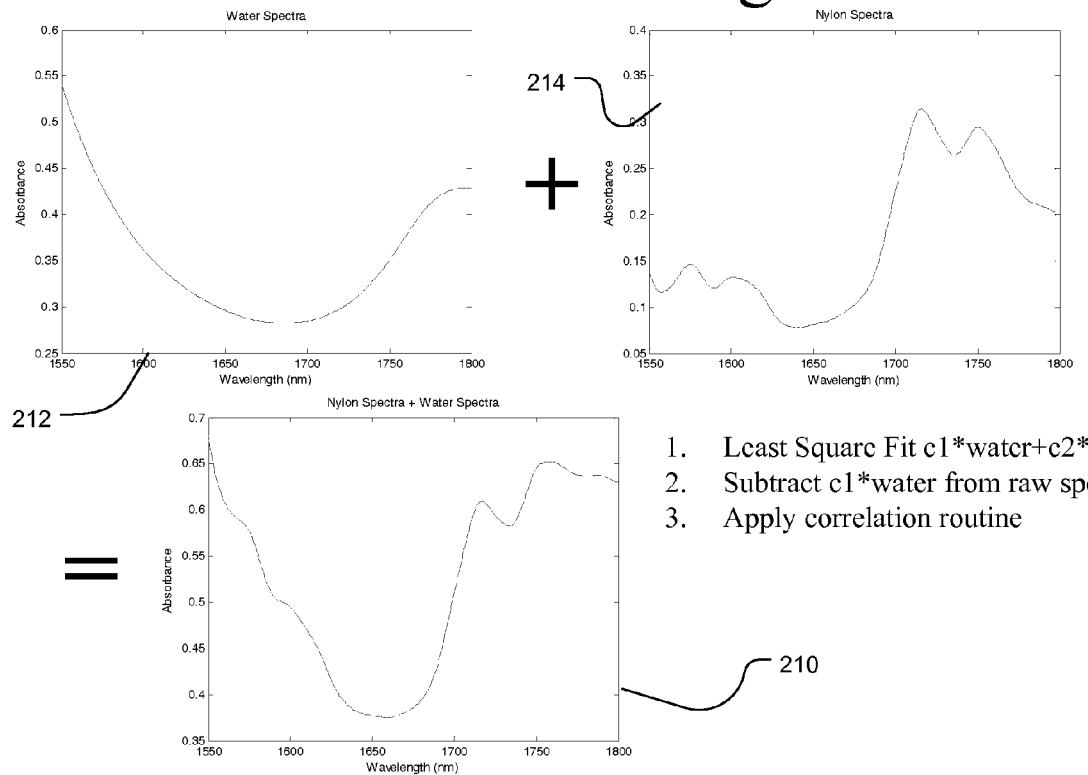
FIG. 6 illustrates a calibration routine used by the tunable laser spectroscopic carpet identification system according to the present invention.

FIG. 6 illustrates a calibration route used by the carpet ID system to compensate for moisture in the carpet. Often, the carpet that is removed has a high moisture content because of moisture damage, which originally necessitated the removal of the carpet. Thus, in the preferred embodiment, the system subtracts a known water spectrum from the detected spectrum. In this way, the system removes the contribution of the water contained in the wet carpet to thereby enable a more accurate identification of the type of material in the carpet under question.

The composite raw spectrum 210 is detected, which comprises a certain amount of water spectral response 212 and nylon, for example, spectra 214. A least squares fit for the equation c1*water+c2*nylon is found. Then the c1*water spectrum is subtracted from raw composite spectra 210. A correlation routine is then applied to the remaining response 214. That is the correlation between the detection spectrum and the spectra of each of nylon 6, nylon 6,6 PET, polypropylene, and wool are determined. If no strong correlation is found with any of the model spectra, the system 100 indicates that the sample should be rescanned, otherwise, the spectra with the highest correlation is reported.

In one example operation, the carpet ID system is used at the point of carpet removal to identify the type of carpet. For example, the system is carried by the carpet removal team to the office building or home where the carpet is to be replaced. The carpet is removed and scanned to determine the type of carpet with the system. Then the carpet is labeled, such as with a machine-readable barcode label generated by a label printer on the system. The label, identifying the type of carpet, is then placed on the carpet bundle or on a truck or associated with the truck that carries the removed carpet to the recycling center. Then, at the recycling center, the barcode or other machine-readable code is read and entered into the recycling system's inventory system to thereby identify the carpet carried on that truck to the inventory system of the recycling center.

In another example, the data regarding the carpet composition is logged to a host computer 65 by the core 61 of the analyzer 60 (see FIG. 4). The connection is wireless in one example. Further in another example, the host computer accesses the ideal or calibration spectra (see FIG. 2) stored in the analyzer to update the spectra to enable analysis and identification of new materials and even non-carpet materials, provide a generic substance identification capability.

Figure 7:
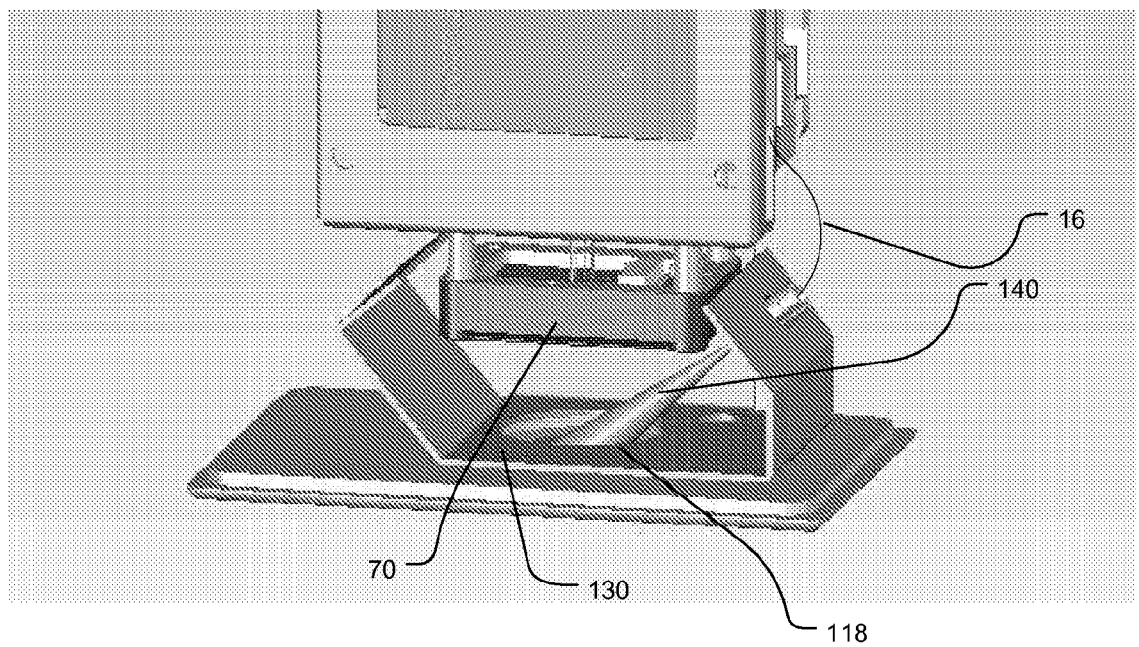
FIG. 7 is a perspective view of a sampling interface of the inventive tunable laser spectroscopic carpet identification system.

FIG. 7 shows the sampling interface in which the housing 110 of the system has been removed. The optical port 118 is illuminated with a 15 millimeter (mm) spot using divergence from a single-mode fiber 16 from the tunable laser 50. Diffusely reflected light is collected with a 3 millimeter (mm) InGaAs detector 142. A window in the port 118 is AlON, aluminum oxynitride, $((AlN)_x \cdot (Al_2O_3)_{1-x}$, mole fraction $0.30 \leq x \leq 0.37)$, to avoid birefringence.

While this invention has been particularly shown and described with references to preferred embodiments thereof, it will be understood by those skilled in the art that various changes in form and details may be made therein without departing from the scope of the invention encompassed by the appended claims.

What is claimed is:

1. A tunable laser spectroscopic carpet identification system, comprising:
    a tunable laser spectroscopy system for generating a tunable signal that is transmitted to a carpet sample and detecting the tunable signal after interaction with the carpet sample, wherein the spectroscopy system comprises:
        a laser cavity in which the tunable signal is generated;
        a semiconductor gain medium in the laser cavity; and
        a tunable element for controlling a wavelength of tunable signal generated in the laser cavity; and
    an analyzer for relating a spectral response of the carpet sample to a chemical composition of the carpet sample, wherein the analyzer estimates a water content of the carpet sample and determines the chemical composition of the carpet sample in part based on the estimate of the water content.

2. A system as claimed in claim 1, wherein the semiconductor gain medium comprises a semiconductor optical amplifier.

3. A system as claimed in claim 1, wherein the semiconductor gain medium comprises a reflective semiconductor optical amplifier.

4. A system as claimed in claim 1, wherein the tunable element comprises a Fabry-Perot tunable filter.

5. A system as claimed in claim 1, wherein the tunable element comprises a microelectromechanical system (MEMS) Fabry-Perot tunable filter.

6. A system as claimed in claim 1, wherein the analyzer estimates the water content of the carpet sample using the spectral response of the carpet sample.

7. A system as claimed in claim 1, wherein a scan band of the tunable signal generated by the tunable laser spectroscopy system extends from about 1550 to 1800 nanometers.

8. A system as claimed in claim 1, wherein a scan band of the tunable signal generated by the tunable laser spectroscopy system extends from about 1600 nanometer to about 1775 nanometers.

9. A system as claimed in claim 1, wherein a scan band of the tunable signal generated by the tunable laser spectroscopy system extends over wavelengths greater than 1700 nanometers.

10. A spectroscopic carpet identification system, comprising:
    a spectroscopy system for determining a spectral response of a carpet sample; and
    an analyzer for relating the spectral response of the carpet sample to a chemical composition of the carpet sample, wherein the analyzer estimates a water content of the carpet sample using the spectral response of the carpet sample and then determines the chemical composition of the carpet sample in part based on the estimate of the water content.

11. A system as claimed in claim 10, wherein the spectroscopy system comprises a tunable laser, comprising a semiconductor gain medium, that generates a tunable signal for illuminating the carpet sample.

12. A system as claimed in claim 10, wherein a scan band of the tunable signal generated by the tunable laser extends from about 1550 to 1800 nanometers.

13. A system as claimed in claim 10, wherein a scan band of the tunable signal generated by the tunable laser extends from about 1600 nanometer to about 1775 nanometers.

14. A system as claimed in claim 10, wherein a scan band of the tunable signal generated by the tunable laser extends over wavelengths greater than 1700 nanometers.

15. A spectroscopic carpet identification method, comprising:
    determining a spectral response of a carpet sample;
    determining a water content of the carpet sample; and
    using the determined water content and the spectral response of the carpet sample to determine a chemical composition of the carpet sample.

16. A method as claimed in claim 15, wherein the step of determining the spectral response comprises:
    generating a tunable signal with a semiconductor gain medium; and
    detecting the tunable signal after interaction with the carpet sample.

17. A method as claimed in claim 15, wherein the step of determining the water content of the carpet sample comprises:
    determining the water content by analysis of the spectral response of the carpet sample.

18. A method as claimed in claim 17, wherein the step of using the determined water content and the spectral response of the carpet sample to determine the chemical composition of the carpet sample comprises subtracting a spectral contribution of water, which is determined based on the determined water content, from the spectral response of the carpet sample to generate a remaining response and then correlating the remaining response to spectra of potential chemical compositions of the carpet sample.

19. A system as claimed in claim 6, wherein the analyzer determines the chemical composition of the carpet sample, in part, based on the estimate of the water content by subtracting a spectral contribution of water, which is determined based on the determined water content, from the spectral response of the carpet sample to generate a remaining response and then correlates the remaining response to spectra of potential chemical compositions of the carpet sample.

* * * * *